United States Patent
Wasdyke et al.

(10) Patent No.: US 9,814,557 B2
(45) Date of Patent: Nov. 14, 2017

(54) STENT PROTECTOR DESIGN

(75) Inventors: Joel Wasdyke, Eden Prairie, MN (US); Michael D. Johnson, Plymouth, MN (US); Shawn Sorenson, Maple Grove, MN (US); Raymond Adney, Coon Rapids, MN (US); Ram Periakaruppan, Falcon Heights, MN (US); Matt Heidner, Maple Grove, MN (US); Sean McNulty, Minneapolis, MN (US); Pu Zhou, Maple Grove, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 2107 days.

(21) Appl. No.: 11/545,253

(22) Filed: Oct. 10, 2006

(65) Prior Publication Data

US 2008/0086192 A1  Apr. 10, 2008

(51) Int. Cl.
*A61M 25/01* (2006.01)
*A61F 2/00* (2006.01)
*A61F 2/958* (2013.01)
*A61M 25/00* (2006.01)
*A61F 2/95* (2013.01)

(52) U.S. Cl.
CPC .............. *A61F 2/0095* (2013.01); *A61F 2/95* (2013.01); *A61F 2/958* (2013.01); *A61F 2002/9522* (2013.01); *A61M 25/002* (2013.01)

(58) Field of Classification Search
CPC .......... A61F 2/95; A61F 2/958; A61F 2/0095; A61F 2002/9522; A61M 25/002

USPC ........................ 623/1.11, 1.12, 1.23; 206/364
See application file for complete search history.

(56) References Cited

U.S. PATENT DOCUMENTS

| | | | | |
|---|---|---|---|---|
| 4,627,838 A | * | 12/1986 | Cross et al. | 604/105 |
| 4,880,414 A | * | 11/1989 | Whipple | 604/533 |
| 5,603,698 A | * | 2/1997 | Roberts et al. | 604/104 |
| 5,800,517 A | * | 9/1998 | Anderson | A61F 2/958 604/171 |
| 5,893,868 A | | 4/1999 | Hanson et al. | 606/198 |
| 6,030,407 A | | 2/2000 | Eidenschink | |
| 6,132,450 A | | 10/2000 | Hanson et al. | 606/198 |
| 6,152,944 A | | 11/2000 | Holman et al. | 606/194 |
| 6,416,529 B1 | * | 7/2002 | Holman et al. | 606/194 |
| 6,554,841 B1 | * | 4/2003 | Yang | 606/108 |
| 6,613,067 B1 | * | 9/2003 | Johnson | 606/194 |
| 6,764,504 B2 | | 7/2004 | Wang et al. | 623/1.11 |
| 6,783,542 B2 | | 8/2004 | Eidenschink | 623/1.11 |
| 6,984,244 B2 | * | 1/2006 | Perez | A61F 2/07 604/103.05 |
| 6,991,639 B2 | | 1/2006 | Holman et al. | 606/194 |
| 7,096,554 B2 | | 8/2006 | Austin et al. | 29/282 |
| 7,316,708 B2 | * | 1/2008 | Gordon et al. | 623/1.11 |
| 2001/0001128 A1 | | 5/2001 | Holman et al. | 623/1.11 |
| 2003/0093086 A1 | | 5/2003 | Briggs et al. | |

(Continued)

*Primary Examiner* — Diane Yabut
(74) *Attorney, Agent, or Firm* — Seager, Tufte & Wickhem, LLP

(57) ABSTRACT

A catheter assembly comprises a catheter having a distal end and a longitudinal axis, a stent disposed about the distal end of the catheter, and a stent protector. The stent protector has a stent covering portion disposed about the stent and a catheter engagement portion that removably engages the stent protector to the catheter assembly. The stent covering portion is disposed about the stent without substantially engaging the stent.

12 Claims, 9 Drawing Sheets

(56) References Cited

U.S. PATENT DOCUMENTS

| | | | |
|---|---|---|---|
| 2004/0093005 A1* | 5/2004 | Durcan | 606/194 |
| 2004/0153122 A1* | 8/2004 | Palermo | A61B 17/068 606/213 |
| 2004/0199239 A1 | 10/2004 | Austin et al. | 623/1.11 |
| 2005/0033404 A1 | 2/2005 | Eidenschink | 623/1.11 |
| 2005/0049671 A1 | 3/2005 | Wang et al. | 623/1.12 |
| 2005/0218022 A1* | 10/2005 | Cervantes | A61F 2/0095 206/363 |
| 2006/0067974 A1 | 3/2006 | Labrecque et al. | 424/426 |
| 2008/0015674 A1* | 1/2008 | Austin et al. | 623/1.11 |

* cited by examiner

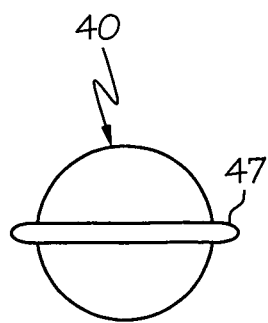 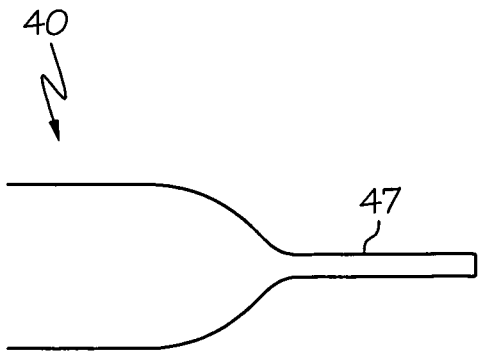
FIG. 10a    FIG. 10b
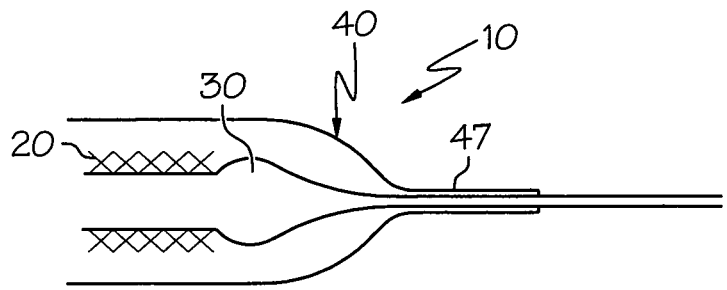
FIG. 11
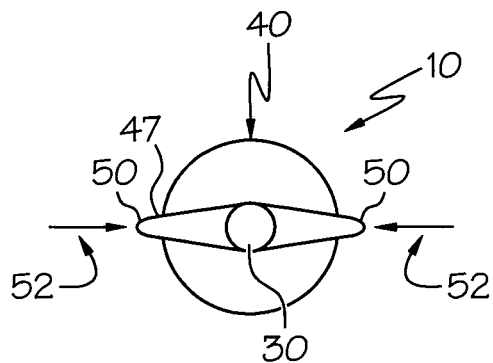 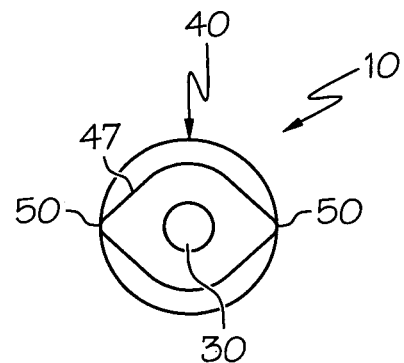
FIG. 12a    FIG. 12b

STENT PROTECTOR DESIGN

CROSS-REFERENCE TO RELATED APPLICATIONS

Not Applicable

STATEMENT REGARDING FEDERALLY SPONSORED RESEARCH

Not Applicable

FIELD OF THE INVENTION

This invention relates to catheter assemblies which are utilized in the delivery of implantable medical devices such as stents and to stent protectors employed on such devices.

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer can enter the body from an access location outside the body, such as through the patient's skin, or by a "cut down" technique in which the entry vessel is exposed by minor surgical means.

Stents and similar devices such as stent-grafts, expandable frameworks, and similar implantable medical devices, are radially expandable endoprostheses which are typically intravascular implants capable of being implanted transluminally and enlarged radially after being introduced percutaneously. Stents can be implanted in a variety of body lumens or vessels such as within the vascular system, urinary tracts, bile ducts, fallopian tubes, coronary vessels, secondary vessels, etc. Stents can be used to reinforce body vessels and to prevent restenosis following angioplasty in the vascular system. They can be self-expanding, expanded by an internal radial force, such as when mounted on a balloon, or a combination of self-expanding and balloon expandable (hybrid expandable).

Stent protectors are used to protect the stent before the stent and catheter assembly are implanted into a body lumen. The stent protectors protect the stent from physical damage or contamination due to the transfer of unwanted material and are removed at the time of use to permit deployment of the stent. Examples of stent protectors are provided in U.S. Pat. No. 6,152,944 and U.S. Pat. No. 6,783,542.

Stent protectors have relied on a friction fit between the stent and the stent protector in order to hold the protector in place. However such intimate contact may not always be desirable. Stents are often used as a vehicle for delivering therapeutic agents (e.g. in the form of a coating on the stent). When removing the stent protector the friction fit could result in therapeutic agent being scraped off. In addition material from the stent protector can also be deposited onto the stent.

Without limiting the scope of the invention a brief summary of some of the claimed embodiments of the invention is set forth below. Additional details of the summarized embodiments of the invention and/or additional embodiments of the invention can be found in the Detailed Description of the Invention below.

BRIEF SUMMARY OF THE INVENTION

The invention is directed to stent protectors that are constructed to reduce or eliminate contact between the stent and the stent protector.

In some embodiments, the invention is a catheter assembly which comprises a catheter having a distal end and a longitudinal axis, a stent disposed about the distal end of the catheter, and a stent protector having a stent covering portion disposed about the stent and a catheter engagement portion. The catheter engagement portion of the stent protector provides engagement of the stent protector to the catheter remote from the stent so that the stent protector does not substantially engage the stent. In some embodiments the engagement location of the stent protector to the catheter is distal to the stent, in others it is proximal to the stent, in still others engagement is provided both distally and proximally of the stent.

In some embodiments, the catheter has raised portions to which the catheter engagement portion of the stent protector is engaged.

In some embodiments, the stent protector supports a portion of the catheter between proximal and distal support structures in the stent protector such that the stent does not contact the stent protector.

These and other embodiments of the invention are described and illustrated in the Drawings and the Detailed Description of the Invention below and/or are characterized in the claims annexed hereto.

BRIEF DESCRIPTION OF THE SEVERAL VIEWS OF THE DRAWING(S)

A detailed description of the invention is hereafter described with specific reference being made to the drawings.

Figure 8A:
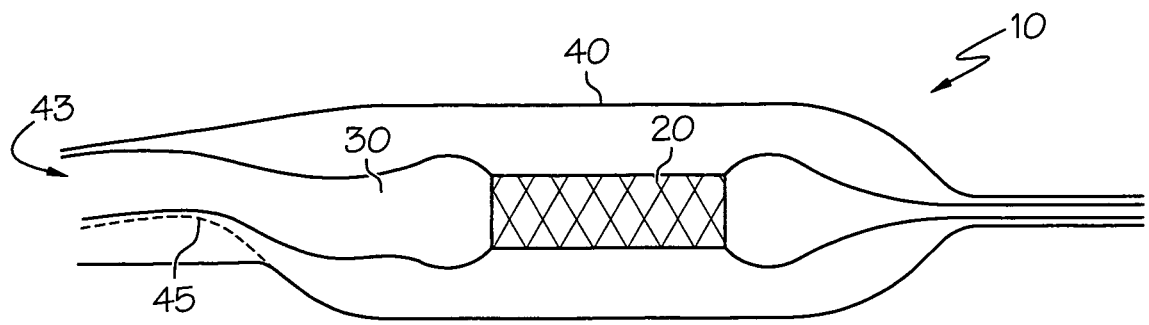
Figure 8B:
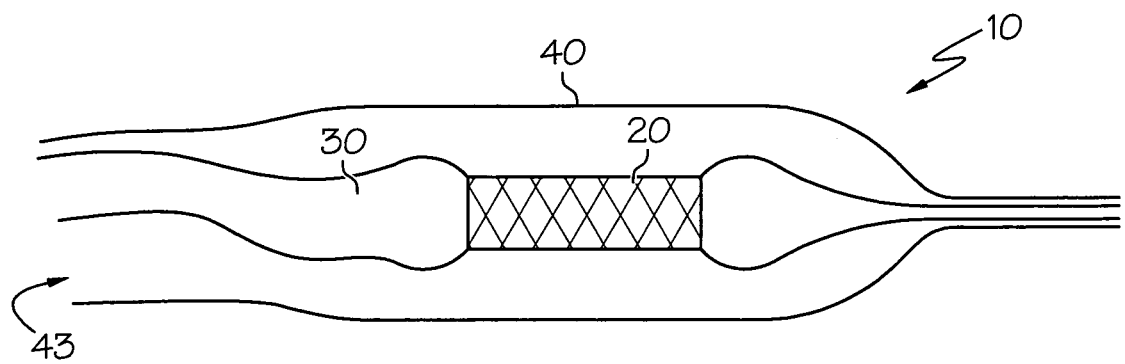

FIGS. 8a-b are schematic side views of a catheter assembly portion having an embodied stent protector disposed about a catheter assembly.

Figure 9A:
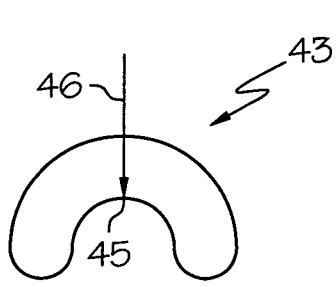
Figure 9B:
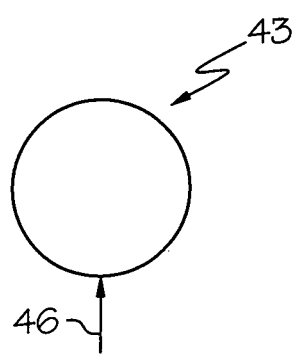

FIGS. 9a-b are views of the open end of the stent protector of FIGS. 8a-b.

FIG. 10a is a distal end view of an alternate embodiment stent protector.

FIG. 10b is a side view of the stent protector of FIG. 10a.

FIG. 11 is a fragmentary side section view of a catheter assembly having the embodied stent protector of FIG. 10a disposed about a catheter.

FIGS. 12a-b are distal end views of a catheter assembly having an embodied stent protector.

Figure 13:
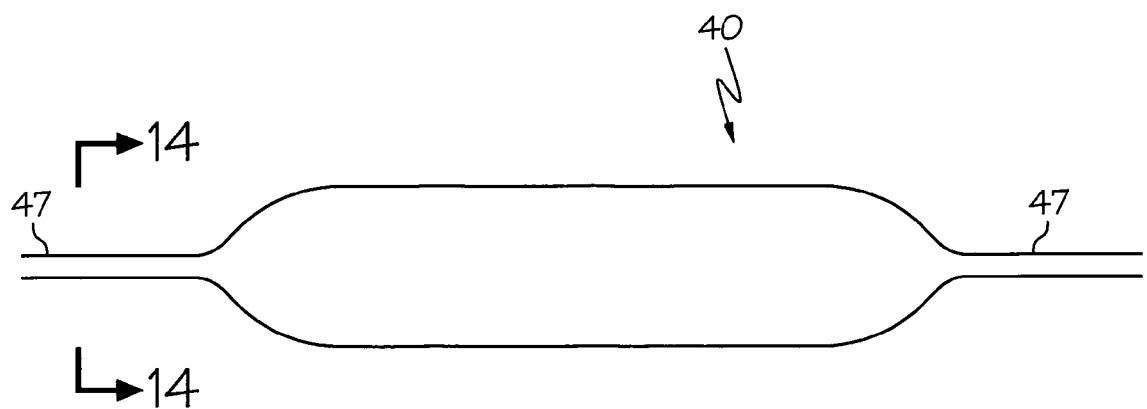

FIG. 13 is a side view of an embodied stent protector.

Figure 14:
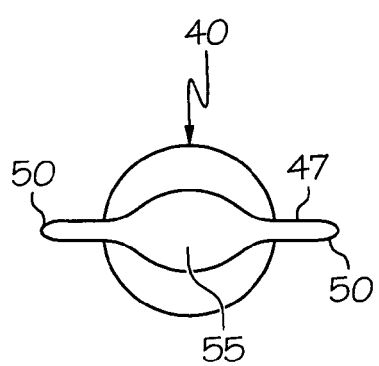
Figure 15:
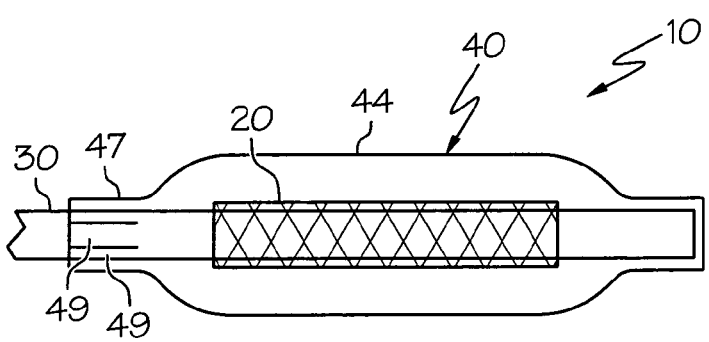

FIG. 14 is a section view of the embodied stent protector of FIG. 13 taken along line A-A FIG. 15 is a schematic side view of a catheter assembly having an embodied stent protector having petals.

Figure 16A:
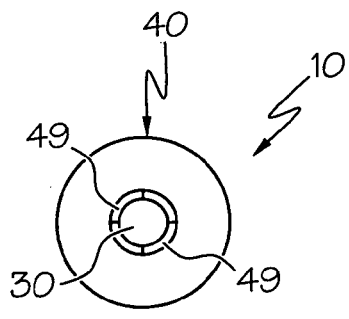
Figure 16B:
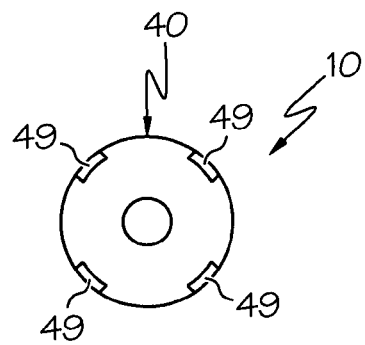

FIGS. 16a-b are section views of a catheter assembly having the embodied stent protector of FIG. 15, viewing the proximal end of the stent protector.

Figure 17:
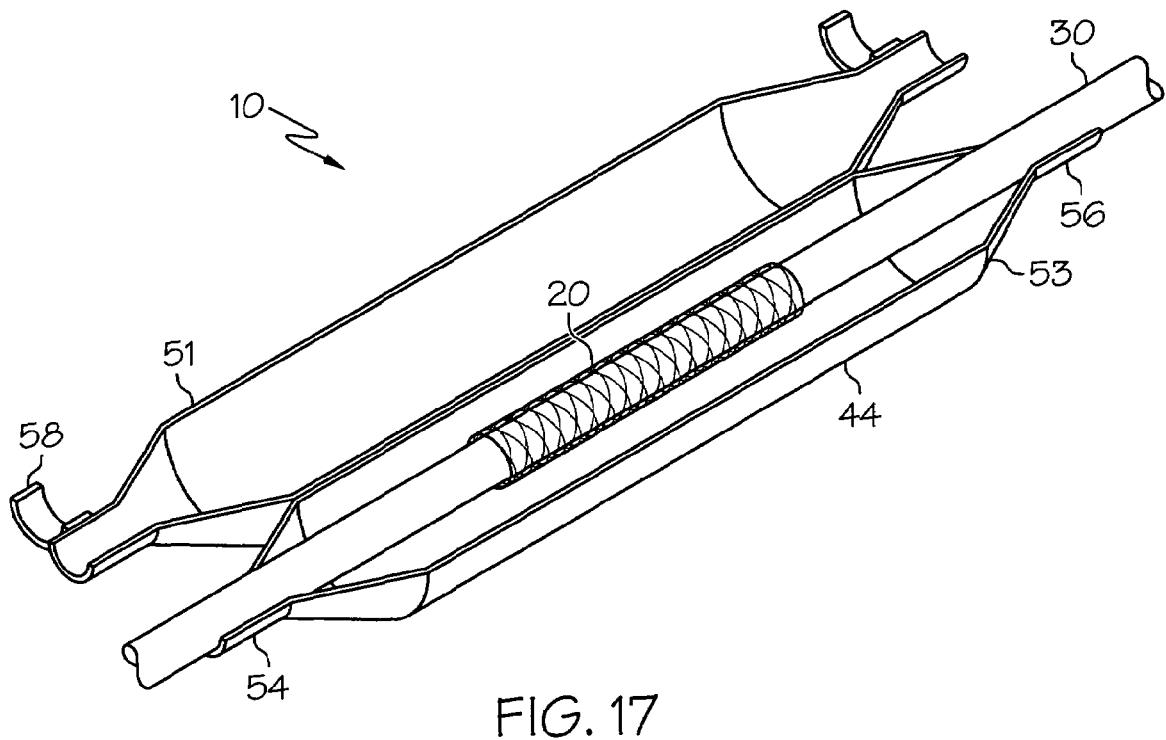

FIG. 17 is a perspective view of a catheter assembly having an embodied stent protector.

Figure 18A:

FIG. 18a is a side of a catheter assembly having the embodied stent protector of FIG. 17.

Figure 18B:
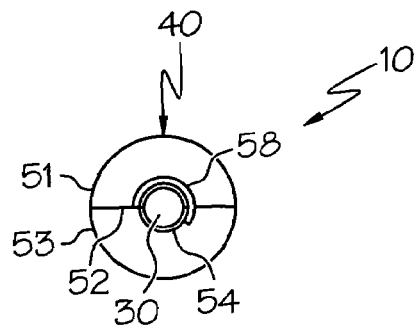

FIG. 18b is a section view of a catheter assembly having the embodied stent protector of FIG. 17 viewing the proximal end of the stent protector.

Figure 19:
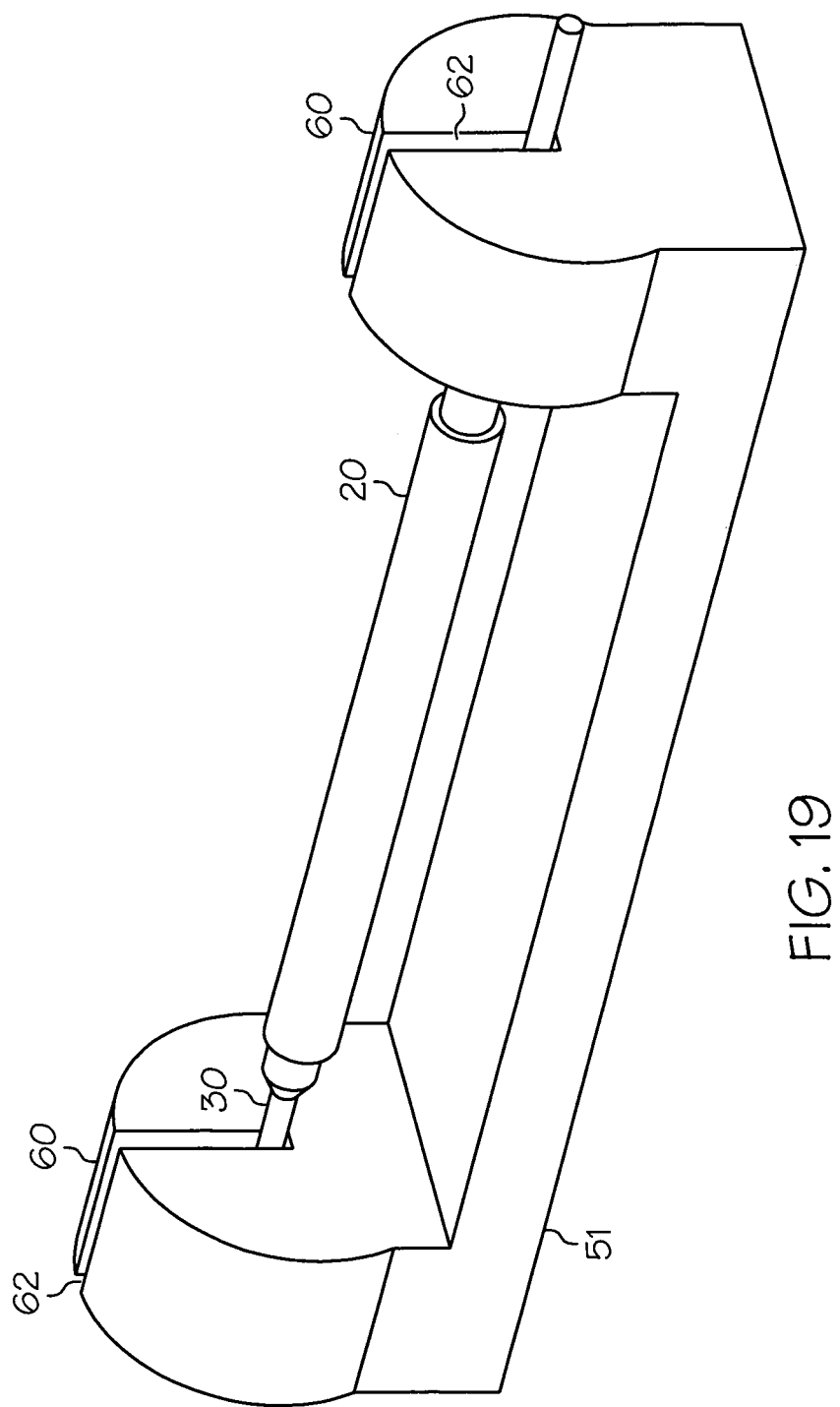

FIG. 19 is a perspective view of the base of an embodied stent protector suspending a portion of a catheter and a stent.

Figure 20:
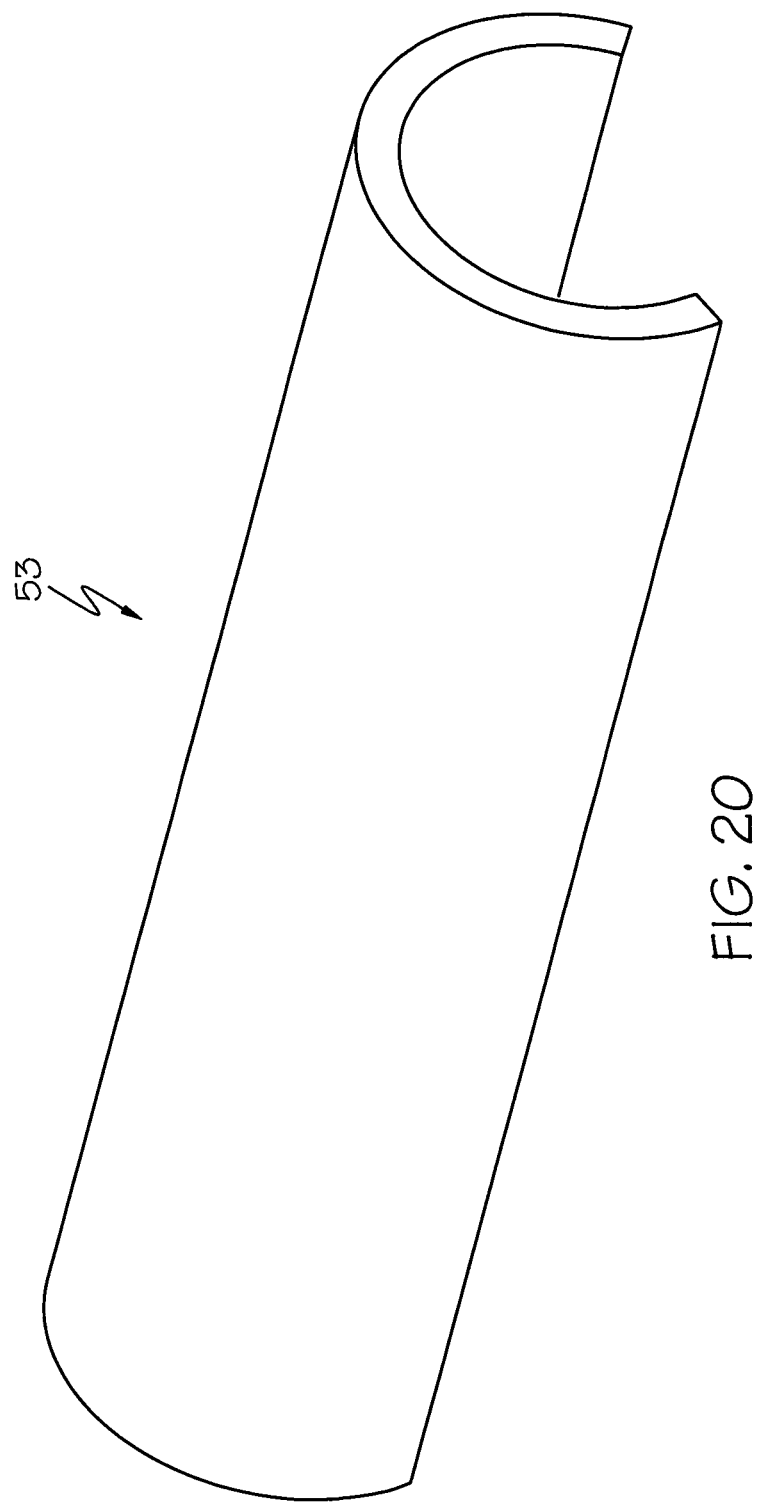

FIG. 20 is a perspective view of the cap of an embodied stent protector.

Figure 21:
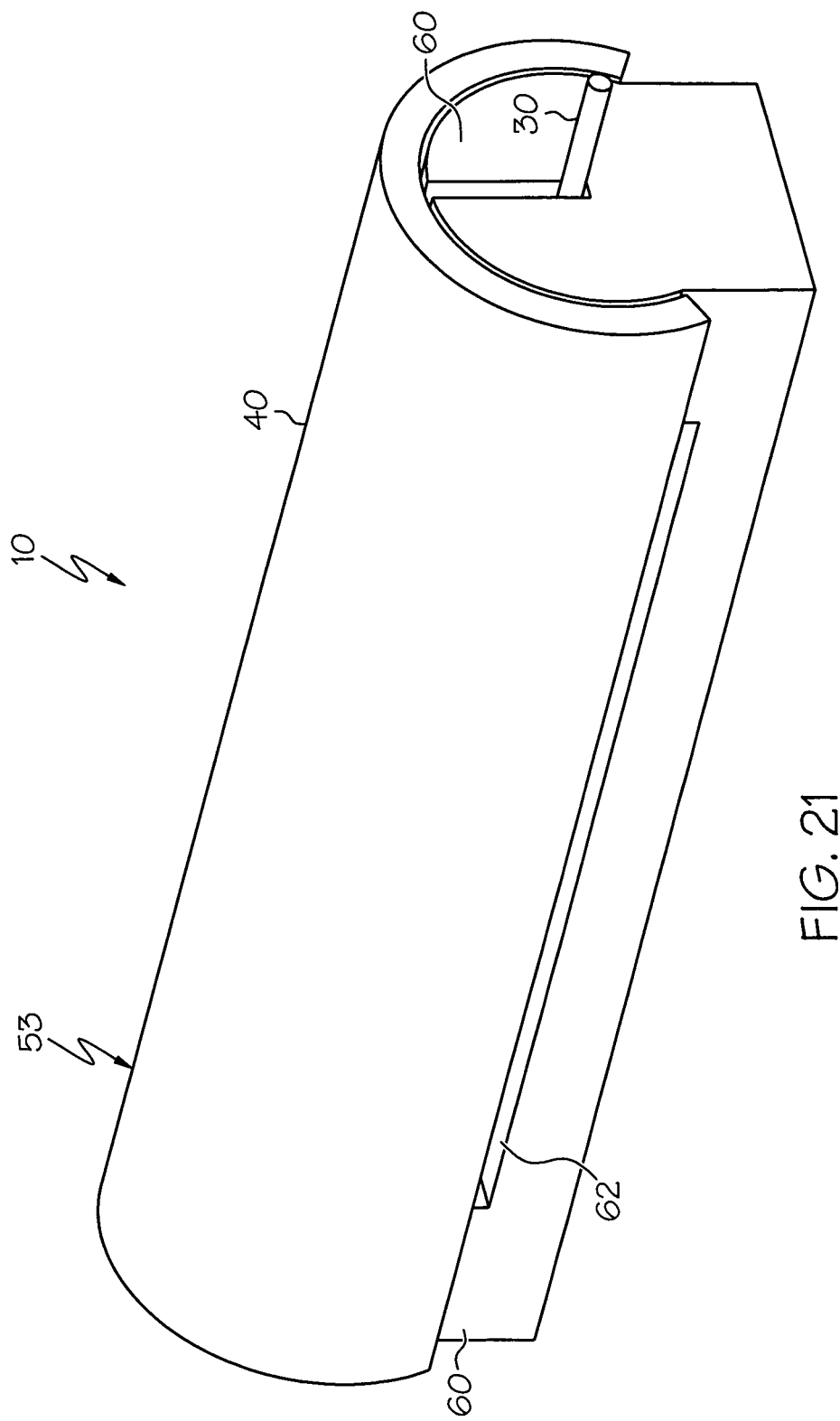

FIG. 21 is a perspective view of a catheter assembly having an embodied stent protector.

DETAILED DESCRIPTION OF THE INVENTION

While this invention can be embodied in many different forms, there are described in detail herein specific preferred embodiments of the invention. This description is an exemplification of the principles of the invention and is not intended to limit the invention to the particular embodiments illustrated. The stent protectors disclosed herein can be used for any type of stent (e.g. peripheral stents, bifurcated stents, and drug-eluting stents).

All US patents and applications and all other published documents mentioned anywhere in this application are incorporated herein by reference in their entirety.

As used in the present application, the stent is not substantially engaged if any contact forces between the stent protector and the stent are less than those which occur between the stent protector and an engagement site on the catheter assembly remote from the stent. Suitably, any contact between the stent protector and the stent does not apply enough frictional or compressive force to disrupt a coating on the stent. Contact which occurs only during removal of the stent protector is not considered engaging contact, although in at least some embodiments of the invention the stent protector does not contact the stent at all while in place as part of the protective assembly and the stent protector can also be easily removed from the catheter without contacting the stent.

For the purposes of this disclosure, like reference numerals in the figures shall refer to like features unless otherwise indicated.

Figure 1:
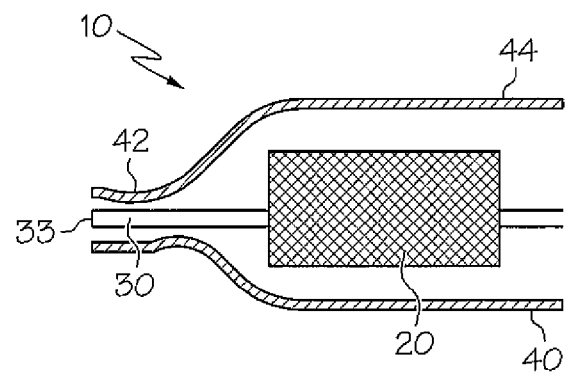
FIGS. 1-2 are schematic side section views of inventive stent protectors disposed about a stent.
Figure 2:
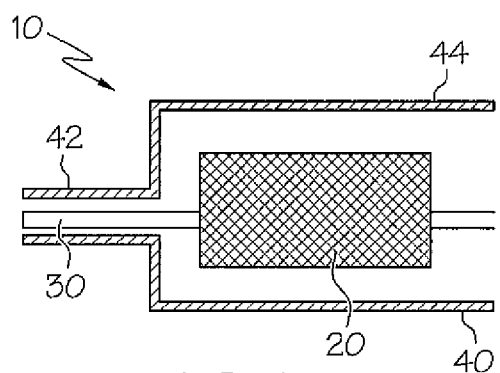

FIGS. 1 and 2 depict catheter assemblies 10 having a stent 20 disposed about the distal end of a catheter 30 and a stent protector 40 disposed about the stent 20. The stent protectors 40 have a narrowed portion 42 at the distal end engaging the catheter distal of the stent. In FIG. 1, moving proximally of portion 42 the stent protector progressively widens to an enlarged diameter in portion 44. In FIG. 2 the diameter changes to portion 44 in a more abrupt step-up manner.

In both cases the enlarged diameter portion 44 covers the stent 20 and maintains a space (i.e. the region between the widened wall portion and the stent) between the interior surface of the wall of the widened portion 44 and the stent such that the widened portion does not engage the stent and in at least some embodiments will not contact the stent at all during normal storage or removal.

The stent protector 40 can be designed to be open at its distal end, as shown in FIGS. 1 and 2. Alternatively, the stent protector can have a closed distal end which can be closed around the distal end 33 of catheter 30 so that proximal movement of the stent protector 40 on the catheter 30 is further restricted by the closed end contacting the distal end of the catheter.

The stent protectors 40 of FIGS. 1 and 2 can be slid off the catheter 30 when pulled in a distal direction with reduced friction between the stent protector 40 and stent 20 than would occur if the stent protector did not have a space between the widened portion and the stent.

Figure 3:
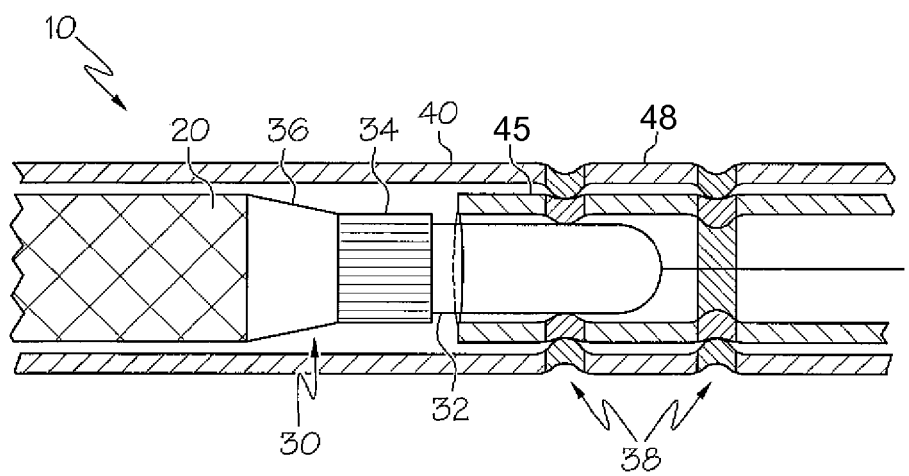
FIG. 3 is a side section view of an embodied stent protector disposed about a catheter assembly.

In another embodiment a stent protector may be formed of two tubes of different diameter, overlapping and attached over a part of their length, but with the larger diameter tube extending beyond the smaller diameter tube and over the stent to form the stent covering portion of the stent protector. The smaller diameter tube provides engagement to the catheter assembly, for instance by frictionally engaging catheter at the catheter's distal tip. FIG. 3 is illustrative.

In FIG. 3 the stent protector 40 comprises an inner tube 45 and an outer tube 48. The inner tube 45 and outer tube 48 are fixed together by adhesive, heat bonding, crimping, or the like. The inner tube 45 fits over the distal end 33 of the catheter 30. In this embodiment the outer tube 48 has a greater length than the inner tube 45 and extends proximally to cover the stent 20. Crimping the inner and outer tubes 45, 48 together can be used to attach the two tubes together and at the same time reduce the diameter of the inner tube 45 to create a friction fit with the catheter.

The inner tube 45 can be of a length such that the proximal end of the inner tube does not extend to the distal edge of the stent thereby preventing contact between the inner tube 45 and the stent 20. In some embodiments the inner tube fits over a catheter tip 32 that contacts one or more distal heat stakes or crimps 37, 38. In FIG. 3 the distal crimp 38 can extend inwardly enough to restrict distal movement of the catheter tip 32 within the inner tube 45.

In some embodiments, the catheter 30 has a marker band 34 and/or balloon edge 36 that has a diameter greater than that of the inner tube thereby restricting the proximal edge of the inner tube 45 to movement distal of the distal edge of the stent 20.

The catheter engagement portion of the stent protector is located distally of the stent in the catheter assemblies of FIGS. 1-3. In other embodiments catheter engagement may be located proximally of the stent or at both proximal and distal locations relative to the stent.

In another embodiment the stent protector may be a tubular member having an inner diameter large enough to cover a stent and catheter, without substantially engaging the stent, but which engages an enlarged diameter catheter engagement area on the catheter. In some such embodiments the tubular member compressively engages the catheter engagement area. Removal may be facilitated by providing a longitudinal or spiral slit through the tubular member. In some embodiments the tubular member substantially maintains its diameter from the proximal end to the distal end. In some embodiments a flared or tapered lead-in portion on the proximal and/or distal end of the stent protector can make it easier to place the stent protector over the catheter.

Figure 4A:
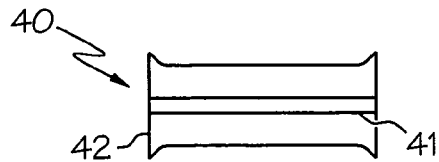
FIGS. 4a-5c are side views of embodied stent protectors having a slit.
Figure 4B:
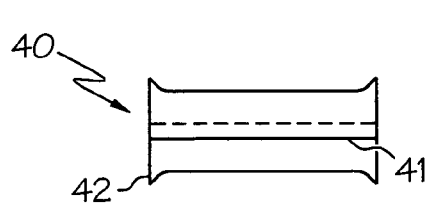
Figure 5A:
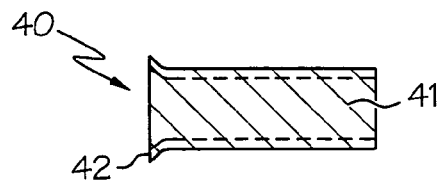
Figure 5B:
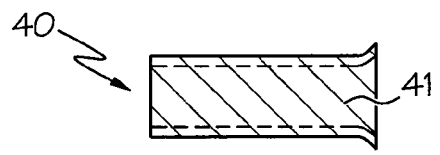
Figure 5C:
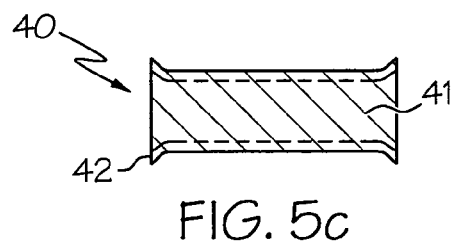
Figure 6:
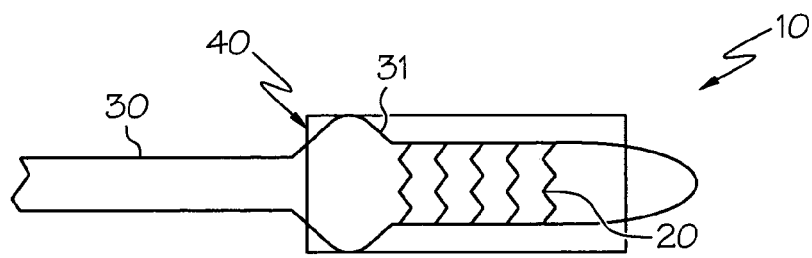
FIG. 6 is a schematic side view of a catheter assembly including the stent protectors of FIGS. 4a-5c disposed about a stent and catheter.

FIGS. 4a-5b illustrate stent protectors 40 for use in the catheter assembly 10 of FIG. 6. The stent protectors comprise a tube 40 having a slit 41 and a flared or tapered portion 42. The stent protector 40 of FIG. 4a-b has a longitudinal slit 41. The slit 41 maintains a space between the edges of the stent protector 40 as shown in FIG. 4a. In some embodiments, the slit allows the edges of the stent protector 40 to contact one another and even overlap as shown in FIG. 4b.

In FIGS. 5a-5c the stent protectors 40 have slits 41 that coil in a longitudinal direction about the stent protector. The stent protector 40 has a flared or tapered lead-in portion 42 on the proximal and/or distal end of the stent protector 40 that can make it easier to place the stent protector 40 over the catheter 30 or can be used when removing the stent protector.

The stent protectors 40 illustrated in FIGS. 4a-5b can be used with the catheter assembly 10 of FIG. 6. The stent protectors 40 contact and engage to the protrusion 31 of catheter 30. The protrusion 31 prevents contraction of the stent protector to the wall of the mounted stent and minimizes any incidental contact that may occur between the stent protector 40 and stent 20. U.S. Pat. No. 6,152,944 discloses other stent protectors that can be used in the catheter assembly 10 of FIG. 6.

Figure 7:
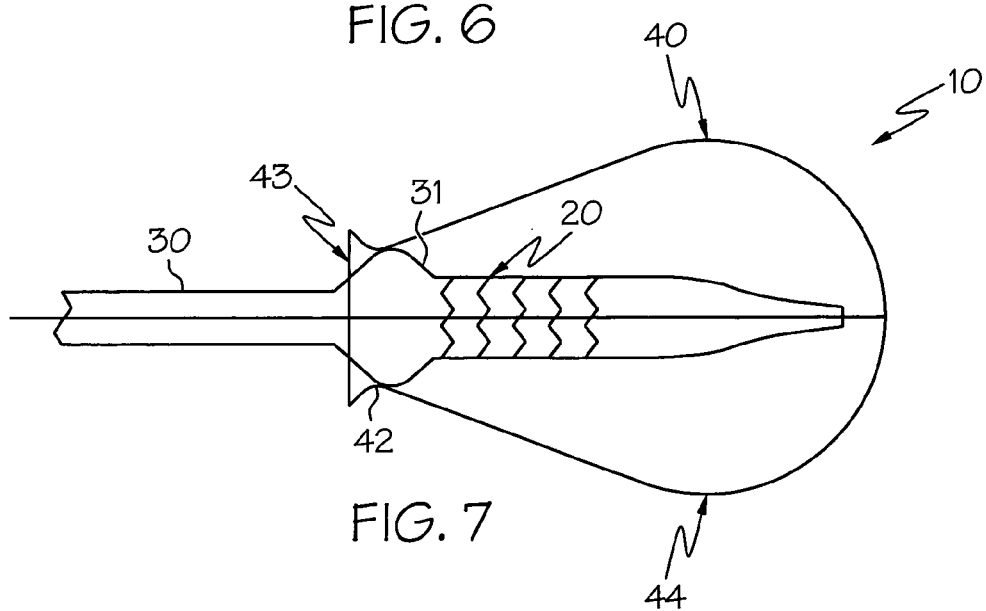
FIG. 7 is a side view of a catheter assembly having an embodied stent protector disposed about a catheter.

FIG. 7 illustrates a catheter assembly 10 having a stent protector 40 that has a hollow bulb design with an opening 43. The hollow bulb has a narrowed portion 42 and a widened portion 44. The narrowed portion 42 engages a raised portion 31 of the catheter 30. The widened portion 44 of the stent protector 40 covers the stent 20 without engaging it. The stent protector 40 can be gripped at the widened portion 44 and pulled distally to remove the stent protector from the catheter without, or with only incidental, contact between the stent protector and the stent 20. It should be noted that the distal end of the stent protector of FIG. 7 has a closed distal end. In other embodiments, not shown, the distal end can be open.

FIGS. 8a-b illustrate a catheter assembly 10 having a stent protector 40 that has a proximal open end 43, the shape of which is reconfigurable. In FIG. 8a the proximal open end 43 of the stent protector 40 has a first size wherein the stent protector 40 is in contact with the catheter 30 and engages it at the dotted line 45. The open end 43 of the stent protector 40 can be reconfigured to a larger second size by forcing the open end to a larger configuration as shown in FIG. 8b. The larger second size of the stent protector 40 allows the stent protector 40 to be removed from the catheter without engaging the stent. In FIGS. 9a-b a transition between an embodied proximal open end 43 is shown in cross-section. Corresponding to FIG. 8a, FIG. 9a shows the smaller configuration as crescent shaped and having small radius 45. Application of radially outward pressure in the direction of the arrow 46 will cause the opening 43 to adopt the open configuration of FIG. 9b which corresponds to FIG. 8b and illustrates the larger configuration as substantially circular. Application of radially inward pressure in the direction of the arrow 46 as shown in FIG. 9b will cause the opening 43 to return to the configuration of FIG. 9a.

The stent protector in FIGS. 8a-9b can be bi-stable in that the larger configuration and the smaller configuration of the smaller catheter engagement portion are stable positions and those positions between the two positions are unstable. Spring metal materials, a number of crosslinked plastics, and some engineering thermoplastic resins can be configured in this way. It should be noted that other shaped openings can be used other than those illustrated in FIGS. 8a-9b. The stent protector 10 can also have stable configurations over a wide variety of positions between those shown in FIGS. 9a and 9b.

In FIGS. 10a-b a stent protector 40 is shown. The stent protector has a catheter engagement portion 47 formed by flattening the distal end of stent protector 40. In the catheter assembly 10 of FIG. 11 the stent protector 40 is engaged to a catheter 30. The flattened distal end 47 frictionally grips the catheter 30. The stent protector 40 can be pulled distally to remove it from the catheter 30. The stent covering portion 44 is widened in order to prevent engagement of the stent protector 40 to the stent 20.

As shown in FIGS. 12a-b, the catheter engagement portion 47 of the stent protector can have squeeze points that are squeezed together to release the stent protector from the catheter 30. In FIG. 12a the catheter engagement portion 47 of stent protector 40 grips catheter 30 thereby engaging the stent protector to the catheter. By applying a force 52 to squeeze points 50 the cross-sectional area of catheter engagement portion 47 is increased, as shown in FIG. 12b. The stent protector 40 can then be removed from the catheter 30. Elastomers, such as silicones, elastomeric polyurethanes and thermoplastic elastomers, and various plastic foam materials may be suitable materials for such embodiments of the invention.

The catheter engagement portion 47 as illustrated in FIGS. 12a-b can be used on one or both of the proximal end and distal end of the stent protector 40. An embodiment with engagement portion 47 located both proximally and distally of the stent is shown in FIG. 13. The proximal catheter engagement portion 47 in some embodiments as shown in FIG. 14 can be wider than the distal catheter engagement portion in order to better accommodate the stent and catheter as it is inserted through the opening 55 upon squeezing the squeeze points 50 together.

As shown in FIG. 15 the stent protector 40 of catheter assembly 10 has a catheter engagement portion 47 having petals 49. The petals 49 can be formed by slitting the catheter engagement portion 47 far enough that when the petals 49 are separated and expanded radially the stent and catheter can pass through the diameter without the stent 20 engaging or contacting the stent protector 40. In FIG. 16a the petals 49 engage the catheter 30. Upon being separated and expanded radially as shown in FIG. 16b, the stent protector 40 is released from the catheter 30. In some embodiments the petals will have a shape memory so that the engaged and expanded position of the petals are bi-stable.

FIGS. 17-21 pertain to a catheter assembly wherein a portion of the catheter is supported within the stent protector. The stent is disposed about the catheter between a proximal and a distal catheter engagement portion of the stent protector.

In FIGS. 17-18b the stent protector 40 has a clam shell design. The clam shell has a first section 51 and a second section 53 which mate along edges 52 when closed. The stent protector 40 supports a portion of a catheter 30 between proximal and distal support structures 54, 56. The catheter has a stent 20 mounted therein which is located between the support struts 54, 56. The stent protector 40 is designed to fold over the portion of the catheter and stent 20 between the proximal and distal supports 54, 56 such that widened portion 44 of the stent protector covers the stent without contacting it. It should be noted that, while illustrated as half-sections, in other embodiments the first section and the second section can vary greatly in size to one another.

A clam shell stent protector optionally can have clasps 58 used for keeping the stent protector closed as shown in FIGS. 18a and 18b which respectively depict side and end views of the stent protector 40 in the closed position. The clasp 58 extends about the support structure 54 to secure the first half 51 and the second half 53 together in the closed position. In some embodiments the clasp 58 extends over a shorter portion of the support structure than illustrated in FIGS. 17-18b; in other embodiments the clasp 58 may extend over a longer portion of the support structure than illustrated in FIGS. 17-18b. In other alternatives a clasp may be centered longitudinally on the device or even extend over the entire device. In some embodiments a clasp may extend over both mating edges 52. In other embodiments the two sections may be hinged along at least a portion of one of the mating edges 52 so that the clasp structure if provided need only extend over a portion or portions of the other mating edge.

As shown in FIGS. 19-21 the stent protector 40 can have a cradle configuration having a base 51 and a cap 53. In FIG. 19 the base 51 includes two supports 60 supporting a catheter 30 with a stent 20 disposed between the supports 60. The catheter can rest within the slots 62. The slots 62 can have a width that closely matches the diameter of the catheter portion disposed therein, thereby frictionally engaging the catheter to the base 51. In some embodiments the supports include clasps or other fasteners to further engage the catheter 30 to the base 51 of the stent protector.

The supports 60 of the base can fittingly engage an optional cap 53, shown in FIG. 20. The cap 53 fits over the supports 60 of base 51; in some embodiments it snaps over the supports. When the cap 53 and base 51 are engaged as illustrated in FIG. 21, the stent 20 is supported between the supports 60 and within the space 62 between the base 51 and the cap 53.

The features of the various figures are illustrative and can be combined in other ways not shown. As non-limiting examples, the catheter engagement mechanism illustrated proximally of the stent in FIG. 6 can be located distally of the stent or both proximally and distally thereof. Likewise a bi-stable engagement mechanism as in FIGS. 9a and 9b, which is proximally of the stent in FIGS. 8a and 8b, can be readily adapted for a distal engagement or for engagements at both proximal and distal locations relative to the stent. The same is true of the petalled engagement mechanism in FIGS. 15, and 16a-b.

The stent protectors as disclosed herein can be formed of a wide variety of polymer materials (e.g. PTFE, FEP, Nylons, silicones, engineering resins, crosslinked resins, thermoplastic elastomers, etc). In some embodiments the stent protector 40 can be formed of braided fiber. In some embodiments the protectors, or portions thereof, may be fabricated of metals, for instance spring metals, or metal/polymer laminates.

In some embodiments the stent, the delivery system or other portion of the assembly can include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. The agent will be in the form of a coating or other layer (or layers) of material in any suitable form placed on a surface region of the stent, which is adapted to be released at the site of the stent's implantation or areas adjacent thereto. Alternately, the therapeutic agent can reside in a reservoir formed within or on the stent using suitable configurations or arrangements. The stent protectors of the invention are especially suited for protecting stents provided with such coatings.

A therapeutic agent can be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent can include but is not limited to: DNA, RNA and their respective derivatives and/or components; hedgehog proteins, etc. Where a therapeutic agent includes cellular material, the cellular material can include but is not limited to: cells of human origin and/or non-human origin as well as their respective components and/or derivatives thereof. Where the therapeutic agent includes a polymer agent, the polymer agent can be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above can be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art can recognize other equivalents to the specific embodiment described herein which equivalents are intended to be encompassed by the claims attached hereto.

The invention claimed is:

1. A catheter assembly comprising:
a catheter having a distal end and a longitudinal axis,
a stent disposed about the distal end of the catheter,
a stent protector having a stent covering portion disposed about the stent and at least one catheter engagement portion, the catheter engagement portion of the stent protector is located distally of the stent, the catheter engagement portion removably engaging the stent protector to the catheter, the stent covering portion is disposed about the stent without substantially engaging the stent, the catheter engagement portion and the stent covering portion comprise the same material layer;
and wherein the stent covering portion of the stent protector and the proximal end of the stent protector have an inner diameter that is larger than that of the catheter engagement portion and larger than an outer diameter of the stent, and the stent protector is free of catheter engagement at the proximal end of the stent protector, the stent protector is configured and arranged to be disengaged from the catheter and is removed from the catheter prior to insertion in a patient's body in a conventional medical procedure.

2. The catheter assembly of claim 1 wherein the stent covering portion of the stent protector does not contact the stent.

3. The catheter assembly of claim 1 wherein the distal end of the catheter has at least one raised portion adjacent to the stent, the at least one raised portion extending radially outward beyond the diameter of the stent, the stent protector engaging the at least one raised portion of the catheter and being held spaced radially apart from the stent.

4. The catheter assembly of claim 1 wherein the stent protector comprises a flared lead-in portion at the proximal end of the stent protector.

5. The catheter assembly of claim 1 wherein the stent protector comprises a tapered lead-in portion at the proximal end of the stent protector.

6. The catheter assembly of claim 1 wherein the stent protector comprises a tapered distal end.

7. The catheter assembly of claim 1 wherein the stent protector comprises slits that coil in a longitudinal direction about the stent protector.

8. A catheter assembly comprising:
   a catheter having a distal end and a longitudinal axis,
   a stent disposed about the distal end of the catheter,
   a stent protector having a stent covering portion disposed about the stent and at least one catheter engagement portion, the catheter engagement portion of the stent protector is located distally of the stent, the stent covering portion comprising a widened proximal end, the catheter engagement portion removably engaging the stent protector to the catheter, the stent covering portion is disposed about the stent without substantially engaging the stent, the catheter engagement portion and the stent covering portion comprise the same material layer;
   and wherein the stent covering portion of the stent protector and the proximal end of the stent protector have an inner diameter that is larger than that of the catheter engagement portion and larger than an outer diameter of the stent, and the stent protector is free of catheter engagement at the proximal end of the stent protector, the stent protector is configured and arranged to be disengaged from the catheter and is removed from the catheter prior to insertion in a patient's body in a conventional medical procedure.

9. The catheter assembly of claim 8 wherein the stent protector comprises a flared lead-in portion at the proximal end of the stent protector.

10. The catheter assembly of claim 8 wherein the stent protector comprises a tapered lead-in portion at the proximal end of the stent protector.

11. The catheter assembly of claim 8 wherein the stent protector comprises a tapered distal end.

12. The catheter assembly of claim 8 wherein the stent protector comprises slits that coil in a longitudinal direction about the stent protector.

* * * * *